United States Patent
Jia et al.

(10) Patent No.: US 8,814,854 B2
(45) Date of Patent: Aug. 26, 2014

(54) CAPSULOTOMY REPAIR DEVICE AND METHOD FOR CAPSULOTOMY REPAIR

(75) Inventors: Guangyao Jia, Irvine, CA (US); Glenn R. Sussman, Laguna Niguel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 845 days.

(21) Appl. No.: 12/754,119

(22) Filed: Apr. 5, 2010

(65) Prior Publication Data

US 2010/0312232 A1 Dec. 9, 2010

Related U.S. Application Data

(63) Continuation-in-part of application No. 12/477,175, filed on Jun. 3, 2009.

(51) Int. Cl.
*A61B 18/14* (2006.01)

(52) U.S. Cl.
USPC .................................. 606/29; 606/45; 606/49

(58) Field of Classification Search
USPC ............................ 606/27–31, 41, 45–50, 166
See application file for complete search history.

(56) References Cited

U.S. PATENT DOCUMENTS

| | | |
|---|---|---|
| 547,867 A | 10/1895 | Taft |
| 560,167 A | 5/1896 | Holmes |
| 974,879 A | 11/1910 | Gwinn |
| 3,159,161 A | 12/1964 | Ness |
| 3,539,034 A | 11/1970 | Woo |
| 3,809,093 A | 5/1974 | Abraham |
| 3,844,272 A | 10/1974 | Banko |
| 3,915,172 A | 10/1975 | Wichterle et al. |
| 3,949,750 A | 4/1976 | Freeman |
| 4,002,169 A | 1/1977 | Cupler, II |
| 4,026,295 A | 5/1977 | Lieberman |
| 4,068,664 A | 1/1978 | Sharp et al. |
| 4,210,146 A | 7/1980 | Banko |
| 4,301,802 A | 11/1981 | Poler |
| 4,315,509 A | 2/1982 | Smit |
| 4,367,744 A | 1/1983 | Sole |
| 4,368,734 A | 1/1983 | Banko |
| 4,425,908 A | 1/1984 | Simon |

(Continued)

FOREIGN PATENT DOCUMENTS

| | | |
|---|---|---|
| CN | 2501478 Y | 7/2002 |
| DE | 3038024 A1 | 4/1982 |

(Continued)

OTHER PUBLICATIONS

Della, Jaymi E., Office Action Summary, U.S. Appl. No. 12/477,175, Feb. 28, 2012, 12 pages.

(Continued)

*Primary Examiner* — Michael Peffley

(57) ABSTRACT

Various embodiments of a capsulotomy repair device include a resistive-heating element comprising an electrically resistive, superelastic wire forming a loop between first and second ends of the superelastic wire. The first and second ends of the loop may at least partially extend at an angle from a planar face defined by the loop, to an insulating portion, to form a transitional neck between the loop and the insulating portion. The capsulotomy repair device may be positioned in the eye relative to a capsularhexis perimeter to overlap tears in the capsularhexis perimeter to remove the tears by forming an adjusted capsularhexis perimeter by burning around the tear.

20 Claims, 16 Drawing Sheets

(56) References Cited

U.S. PATENT DOCUMENTS

| | | | |
|---|---|---|---|
| 4,457,757 A | 7/1984 | Molteno | |
| 4,481,948 A * | 11/1984 | Sole | 606/45 |
| 4,485,816 A | 12/1984 | Krumme | |
| 4,501,274 A | 2/1985 | Skjaerpe | |
| 4,530,356 A | 7/1985 | Helfgott et al. | |
| 4,530,359 A | 7/1985 | Helfgott et al. | |
| 4,531,934 A | 7/1985 | Kossovsky et al. | |
| 4,559,942 A | 12/1985 | Eisenberg | |
| 4,570,632 A | 2/1986 | Woods | |
| 4,607,622 A | 8/1986 | Fritch et al. | |
| 4,616,656 A | 10/1986 | Nicholson et al. | |
| 4,665,906 A | 5/1987 | Jervis | |
| 4,676,243 A | 6/1987 | Clayman | |
| 4,706,669 A | 11/1987 | Schlegel | |
| 4,706,671 A | 11/1987 | Weinrib | |
| 4,708,138 A | 11/1987 | Pazandak | |
| 4,729,761 A | 3/1988 | White | |
| 4,766,896 A | 8/1988 | Pao | |
| 4,766,897 A | 8/1988 | Smirmaul | |
| 4,781,675 A | 11/1988 | White | |
| 4,805,616 A | 2/1989 | Pao | |
| 4,869,248 A | 9/1989 | Narula | |
| 4,869,716 A | 9/1989 | Smirmaul | |
| 4,885,004 A | 12/1989 | Pao | |
| 4,900,300 A | 2/1990 | Lee | |
| 4,911,161 A | 3/1990 | Schechter | |
| 4,936,825 A | 6/1990 | Ungerleider | |
| 4,950,272 A | 8/1990 | Smirmaul | |
| 4,955,859 A | 9/1990 | Zilber | |
| 4,955,894 A | 9/1990 | Herman | |
| 4,986,825 A | 1/1991 | Bays et al. | |
| 4,994,066 A | 2/1991 | Voss | |
| 5,047,008 A | 9/1991 | de Juan, Jr. et al. | |
| 5,085,664 A | 2/1992 | Bozzo | |
| 5,123,906 A | 6/1992 | Kelman | |
| 5,135,530 A | 8/1992 | Lehmer | |
| 5,180,362 A | 1/1993 | Worst | |
| 5,188,634 A | 2/1993 | Hussein et al. | |
| 5,199,445 A | 4/1993 | Rubinfeld | |
| 5,203,865 A | 4/1993 | Siepser | |
| 5,234,436 A | 8/1993 | Eaton et al. | |
| 5,242,404 A | 9/1993 | Conley et al. | |
| 5,242,449 A | 9/1993 | Zaleski | |
| 5,261,923 A | 11/1993 | Soares | |
| 5,269,787 A | 12/1993 | Cozean, Jr. et al. | |
| 5,322,504 A | 6/1994 | Doherty et al. | |
| 5,342,377 A | 8/1994 | Lazserson | |
| 5,346,491 A | 9/1994 | Oertli | |
| 5,360,399 A | 11/1994 | Stegmann | |
| 5,364,405 A | 11/1994 | Zaleski | |
| 5,366,443 A | 11/1994 | Eggers et al. | |
| 5,374,244 A | 12/1994 | Clement et al. | |
| 5,395,361 A | 3/1995 | Fox et al. | |
| 5,411,510 A | 5/1995 | Fugo | |
| 5,413,574 A | 5/1995 | Fugo | |
| 5,423,330 A | 6/1995 | Lee | |
| 5,423,841 A | 6/1995 | Kornefeld | |
| 5,439,474 A | 8/1995 | Li | |
| 5,445,636 A | 8/1995 | Bretton | |
| 5,455,637 A | 10/1995 | Kallman et al. | |
| 5,466,234 A | 11/1995 | Loeb et al. | |
| 5,478,338 A | 12/1995 | Reynard | |
| 5,484,433 A | 1/1996 | Taylor et al. | |
| 5,486,165 A | 1/1996 | Stegmann | |
| 5,486,183 A | 1/1996 | Middleman et al. | |
| 5,487,725 A | 1/1996 | Peyman | |
| 5,509,923 A | 4/1996 | Middleman et al. | |
| 5,522,829 A | 6/1996 | Michalos | |
| 5,527,332 A | 6/1996 | Clement | |
| 5,562,692 A | 10/1996 | Bair | |
| 5,569,197 A | 10/1996 | Helmus et al. | |
| 5,569,280 A | 10/1996 | Kamerling | |
| 5,601,094 A | 2/1997 | Reiss | |
| 5,601,572 A | 2/1997 | Middleman et al. | |
| 5,601,593 A | 2/1997 | Freitag | |
| 5,626,558 A | 5/1997 | Suson | |
| 5,630,827 A | 5/1997 | Vijfvinkel | |
| 5,632,746 A | 5/1997 | Middleman et al. | |
| 5,651,783 A | 7/1997 | Reynard | |
| 5,662,670 A | 9/1997 | Michalos | |
| 5,669,923 A | 9/1997 | Gordon | |
| 5,670,161 A | 9/1997 | Healy et al. | |
| 5,683,592 A | 11/1997 | Bartholomew et al. | |
| 5,700,243 A | 12/1997 | Narciso, Jr. | |
| 5,716,363 A | 2/1998 | Josephberg | |
| 5,720,754 A | 2/1998 | Middleman et al. | |
| 5,728,117 A | 3/1998 | Lash | |
| 5,733,276 A | 3/1998 | Belkin | |
| 5,733,297 A | 3/1998 | Wang | |
| 5,741,244 A | 4/1998 | Klaas | |
| 5,749,879 A | 5/1998 | Middleman et al. | |
| 5,755,731 A | 5/1998 | Grinberg | |
| 5,766,171 A | 6/1998 | Silvestrini | |
| 5,792,166 A | 8/1998 | Gordon et al. | |
| 5,820,628 A | 10/1998 | Middleman et al. | |
| 5,827,321 A | 10/1998 | Roubin et al. | |
| 5,843,019 A | 12/1998 | Eggers et al. | |
| 5,860,994 A | 1/1999 | Yaacobi | |
| 5,865,800 A | 2/1999 | Mirarchi et al. | |
| 5,868,697 A | 2/1999 | Richter et al. | |
| 5,873,883 A | 2/1999 | Cozean, Jr. et al. | |
| 5,885,279 A | 3/1999 | Bretton | |
| 5,888,201 A | 3/1999 | Stinson et al. | |
| 5,891,084 A | 4/1999 | Lee | |
| 5,893,862 A | 4/1999 | Pratt et al. | |
| 5,898,697 A | 4/1999 | Hurme et al. | |
| 5,904,690 A | 5/1999 | Middleman et al. | |
| 5,911,729 A | 6/1999 | Shikhman et al. | |
| 5,921,999 A | 7/1999 | Dileo | |
| 5,925,056 A | 7/1999 | Thomas et al. | |
| 5,957,921 A | 9/1999 | Mirhashemi et al. | |
| 5,989,262 A | 11/1999 | Josephberg | |
| 6,004,330 A | 12/1999 | Middleman et al. | |
| 6,036,688 A | 3/2000 | Edwards | |
| 6,059,792 A | 5/2000 | Josephberg | |
| 6,066,138 A * | 5/2000 | Sheffer et al. | 606/49 |
| 6,135,998 A | 10/2000 | Palanker | |
| 6,142,996 A | 11/2000 | Mirhashemi et al. | |
| 6,162,202 A | 12/2000 | Sicurelli et al. | |
| 6,165,190 A | 12/2000 | Nguyen | |
| 6,179,830 B1 | 1/2001 | Kokubu | |
| 6,203,518 B1 | 3/2001 | Anis et al. | |
| 6,217,598 B1 | 4/2001 | Berman et al. | |
| 6,241,721 B1 | 6/2001 | Cozean et al. | |
| 6,264,668 B1 | 7/2001 | Prywes | |
| 6,306,155 B1 | 10/2001 | Chandler et al. | |
| 6,379,370 B1 | 4/2002 | Feinsod | |
| 6,413,262 B2 | 7/2002 | Saishin et al. | |
| 6,440,103 B1 | 8/2002 | Hood et al. | |
| 6,447,523 B1 | 9/2002 | Middleman et al. | |
| 6,503,263 B2 | 1/2003 | Adams | |
| 6,506,176 B1 | 1/2003 | Mittelstein et al. | |
| 6,544,254 B1 | 4/2003 | Bath | |
| 6,551,326 B1 | 4/2003 | Van Heugten et al. | |
| 6,575,929 B2 | 6/2003 | Sussman et al. | |
| 6,616,996 B1 | 9/2003 | Keith et al. | |
| 6,629,980 B1 | 10/2003 | Eibschitz-Tsimhoni | |
| 6,673,064 B1 | 1/2004 | Rentrop | |
| 6,764,439 B2 | 7/2004 | Schaaf et al. | |
| 6,979,328 B2 | 12/2005 | Baerveldt et al. | |
| 6,986,774 B2 | 1/2006 | Middleman et al. | |
| 7,011,666 B2 | 3/2006 | Feinsod | |
| 7,135,009 B2 | 11/2006 | Tu et al. | |
| 7,585,295 B2 | 9/2009 | Ben-Nun | |
| 7,722,626 B2 | 5/2010 | Middleman et al. | |
| 8,128,641 B2 | 3/2012 | Wardle | |
| 8,162,931 B2 | 4/2012 | Ben-Nun | |
| 8,235,978 B2 * | 8/2012 | Ben-Nun | 606/29 |
| 8,323,276 B2 | 12/2012 | Palanker et al. | |
| 2001/0044625 A1 | 11/2001 | Hata et al. | |
| 2002/0007150 A1 | 1/2002 | Johnson | |

(56) References Cited

U.S. PATENT DOCUMENTS

| | | | |
|---|---|---|---|
| 2002/0049437 A1* | 4/2002 | Silvestrini | 606/41 |
| 2002/0091402 A1 | 7/2002 | Feinsod | |
| 2002/0161365 A1 | 10/2002 | Martins | |
| 2004/0050392 A1 | 3/2004 | Tu et al. | |
| 2004/0092982 A1 | 5/2004 | Sheffer | |
| 2004/0106929 A1 | 6/2004 | Masket | |
| 2004/0116950 A1 | 6/2004 | Eibschitz-Tsimhoni | |
| 2004/0220564 A1 | 11/2004 | Ho et al. | |
| 2005/0054972 A1 | 3/2005 | Adams et al. | |
| 2005/0228419 A1 | 10/2005 | El-Mansoury | |
| 2006/0036270 A1 | 2/2006 | Terao | |
| 2006/0100617 A1 | 5/2006 | Boukhny | |
| 2006/0106370 A1 | 5/2006 | Baerveldt et al. | |
| 2006/0241580 A1 | 10/2006 | Mittelstein et al. | |
| 2006/0259053 A1 | 11/2006 | El-Mansoury | |
| 2007/0010812 A1 | 1/2007 | Mittelstein et al. | |
| 2007/0049957 A1 | 3/2007 | Benitez | |
| 2007/0060926 A1 | 3/2007 | Escaf | |
| 2007/0073275 A1 | 3/2007 | Conston et al. | |
| 2007/0078359 A1 | 4/2007 | Luloh et al. | |
| 2007/0191862 A1 | 8/2007 | Ellis | |
| 2007/0239156 A1 | 10/2007 | Palanker et al. | |
| 2007/0276420 A1 | 11/2007 | Sorensen et al. | |
| 2008/0114341 A1 | 5/2008 | Thyzel | |
| 2009/0054904 A1 | 2/2009 | Holmen | |
| 2009/0094278 A1 | 4/2009 | Andrews | |
| 2009/0137992 A1 | 5/2009 | Nallakrishnan | |
| 2009/0216225 A1 | 8/2009 | Ben-Nun | |
| 2009/0240149 A1 | 9/2009 | Peyman | |
| 2009/0287143 A1 | 11/2009 | Line | |
| 2009/0287233 A1 | 11/2009 | Huculak | |
| 2010/0057069 A1 | 3/2010 | Ben-Nun | |
| 2010/0094278 A1 | 4/2010 | Jia et al. | |
| 2010/0106155 A1 | 4/2010 | Anderson et al. | |
| 2010/0145331 A1 | 6/2010 | Chrisitian et al. | |
| 2010/0145447 A1 | 6/2010 | Jia et al. | |
| 2010/0179544 A1* | 7/2010 | Boukhny et al. | 606/48 |
| 2010/0274272 A1 | 10/2010 | Medina | |
| 2010/0298820 A1 | 11/2010 | Ben-Nun | |
| 2010/0312252 A1 | 12/2010 | Jia et al. | |
| 2011/0054384 A1 | 3/2011 | Brown | |
| 2011/0087256 A1 | 4/2011 | Wiener et al. | |
| 2011/0202049 A1 | 8/2011 | Jia et al. | |
| 2011/0282335 A1 | 11/2011 | Sussman et al. | |
| 2012/0158027 A1 | 6/2012 | Moradian et al. | |
| 2012/0158130 A1 | 6/2012 | Moradian et al. | |
| 2013/0066351 A1 | 3/2013 | Giardina et al. | |
| 2013/0158573 A1 | 6/2013 | Zaidman et al. | |
| 2013/0197548 A1 | 8/2013 | Keller | |

FOREIGN PATENT DOCUMENTS

| | | |
|---|---|---|
| DE | 3205959 A1 | 9/1983 |
| DE | 3248101 A1 | 6/1984 |
| DE | 3434930 A1 | 4/1986 |
| DE | 8710541 U1 | 11/1987 |
| DE | 197 40 530 A1 | 3/1990 |
| DE | 4012882 A1 | 10/1991 |
| DE | 9311879 U1 | 11/1993 |
| DE | 19719549 A1 | 11/1998 |
| DE | 19809510 A1 | 9/1999 |
| DE | 10220253 A1 | 11/2002 |
| EP | 0170650 B1 | 8/1985 |
| EP | 183385 B1 | 3/1989 |
| EP | 165657 B1 | 7/1989 |
| EP | 0335714 A2 | 10/1989 |
| EP | 358990 A1 | 3/1990 |
| EP | 0228185 B1 | 7/1990 |
| EP | 0355341 B1 | 10/1992 |
| EP | 0537116 A1 | 4/1993 |
| EP | 506618 B1 | 7/1995 |
| EP | 0730848 A2 | 9/1996 |
| EP | 0730848 A3 | 7/1997 |
| EP | 0788802 A2 | 8/1997 |
| EP | 0898947 A2 | 3/1999 |
| EP | 0898947 A3 | 9/1999 |
| EP | 0730848 B1 | 4/2000 |
| EP | 0788802 A3 | 4/2000 |
| EP | 1010410 A1 | 6/2000 |
| EP | 1027906 A2 | 8/2000 |
| EP | 0986328 A4 | 5/2001 |
| EP | 1095641 A1 | 5/2001 |
| EP | 0788802 B1 | 7/2006 |
| EP | 1809196 A4 | 3/2008 |
| EP | 1809196 B1 | 9/2010 |
| EP | 1871216 B1 | 6/2012 |
| ES | 2 103 635 | 9/1997 |
| FR | 2544979 A1 | 11/1984 |
| FR | 2588751 A1 | 4/1987 |
| FR | 2 676 355 | 11/1992 |
| FR | 2677244 A1 | 12/1992 |
| FR | 2702955 A1 | 9/1994 |
| FR | 2707872 A1 | 1/1995 |
| FR | 2830186 A1 | 4/2003 |
| FR | 2855745 A1 | 12/2004 |
| FR | 2855746 A1 | 12/2004 |
| FR | 2924924 A1 | 6/2009 |
| GB | 2247174 A | 2/1992 |
| GB | 2437252 A | 10/2007 |
| JP | 2004-523272 | 8/2004 |
| JP | 2007014510 | 1/2007 |
| JP | 2007-83049 | 4/2007 |
| JP | 2008-538306 A | 10/2008 |
| KR | 20100016724 | 2/2010 |
| KR | 20100121583 | 11/2010 |
| KR | 101039394 B1 | 6/2011 |
| KR | 101039398 B1 | 6/2011 |
| RU | 1790934 A1 | 1/1993 |
| RU | 1790935 A1 | 1/1993 |
| SU | 452338 | 12/1974 |
| SU | 1301400 A1 | 4/1987 |
| SU | 1395314 A1 | 5/1988 |
| SU | 1431752 A1 | 10/1988 |
| SU | 1440496 A1 | 11/1988 |
| SU | 1766403 A1 | 10/1992 |
| SU | 1148613 A1 | 4/1995 |
| WO | WO 86/02257 A1 | 4/1986 |
| WO | WO 93/01755 A1 | 2/1993 |
| WO | WO 93/20765 A1 | 10/1993 |
| WO | WO 95/08310 A1 | 3/1995 |
| WO | WO 96/06570 A1 | 3/1996 |
| WO | WO 97/26835 A1 | 7/1997 |
| WO | WO 97/30669 A1 | 8/1997 |
| WO | WO 98/49945 A1 | 11/1998 |
| WO | WO 99/60936 A1 | 12/1999 |
| WO | WO 00/48540 A1 | 8/2000 |
| WO | WO 01/56519 A1 | 8/2001 |
| WO | WO 01/60266 A1 | 8/2001 |
| WO | WO 03/022174 A2 | 3/2003 |
| WO | WO 03/022174 A3 | 3/2003 |
| WO | WO 03/039335 A2 | 5/2003 |
| WO | WO 03/039335 A3 | 5/2003 |
| WO | WO 03/045290 A1 | 6/2003 |
| WO | WO 2004/039295 A1 | 5/2004 |
| WO | WO 2004/071312 A1 | 8/2004 |
| WO | WO 2006/052374 A2 | 5/2006 |
| WO | WO 2006/052374 A3 | 5/2006 |
| WO | WO 2006/109255 A1 | 10/2006 |
| WO | WO 2006/109290 A2 | 10/2006 |
| WO | WO 2006/117772 A1 | 11/2006 |
| WO | WO 2007/121485 A2 | 10/2007 |
| WO | WO 2008/080149 A1 | 7/2008 |
| WO | 2008/115455 | 9/2008 |
| WO | WO 2009/140414 A1 | 11/2009 |
| WO | WO 2009/153550 A1 | 12/2009 |
| WO | WO 2010/044988 A1 | 4/2010 |
| WO | WO 2010/068662 A1 | 6/2010 |
| WO | WO 2010/141179 A1 | 12/2010 |
| WO | WO 2010/141181 A1 | 12/2010 |
| WO | WO 2011/102928 A1 | 8/2011 |
| WO | 2013/022854 A1 | 2/2013 |

(56) References Cited

FOREIGN PATENT DOCUMENTS

| WO | 2013/070423 A1 | 5/2013 |
| WO | 2013/073609 A1 | 5/2013 |

OTHER PUBLICATIONS

International Searching Authority, International Search Report, International Application No. PCT/US2010/033893, Jul. 8, 2010, 5 pages.

International Searching Authority, Written Opinion of the International Searching Authority, International Application No. PCT/US2010/033893, Jul. 8, 2010, 8 pages.

International Searching Authority, International Preliminary Report on Patentability, International Application No. PCT/US2009/057836, Apr. 19, 2011, 7 pages.

International Searching Authority, Written Opinion of the International Searching Authority, International Application No. PCT/US2009/057836, Apr. 19, 2011, 6 pages.

International Searching Authority, International Search Report, International Application No. PCT/US2010/033949, Jul. 23, 2010, 6 pages.

International Searching Authority, Written Opinion of the International Searching Authority, International Application No. PCT/US2010/033949, Jul. 23, 2010, 9 pages.

International Searching Authority, International Search Report, International Application No. PCT/US2011/021608, Mar. 1, 2011, 6 pages.

International Searching Authority, Written Opinion of the International Searching Authority, International Application No. PCT/US2011/021608, Mar. 1, 2011, 9 pages.

Holloway, Ian Knobel, Office Action Summary, U.S. Appl. No. 12/249,982, May 11, 2011, 23 pages.

Della, Jaymi E., Office Action Summary, U.S. Appl. No. 12/477,175, Jun. 18, 2012, 12 pages.

Holloway, Ian Knobel, Office Action Summary, U.S. Appl. No. 12/249,982, Jun. 18, 2012, 7 pages.

Della, Jaymi E., Office Action Summary, U.S. Appl. No. 12/477,175, Nov. 14, 2011, 39 pages.

Bretton, Randolph H. et al., "Use of bipolar diathermy to prevent posterior capsule opacification," Journal of Cataract Refractive Surgery 2002; 2 8:866-878.

Sussman, Glen et al., Capsularhexis Device with Flexible Heating Element having an Angled Transitional Neck, U.S. Appl. No. 12/477,175, filed Jun. 3, 2009, 32 pages.

International Searching Authority, International Preliminary Report on Patentability, PCT/US2005/036670, May 15, 2007, 4 pages.

Huculak, John C. et al., Capsularhexis Device Using Pulsed Electric Fields, U.S. Appl. No. 12/618,805, filed Nov. 16, 2009, 14 pages.

Jia, Guangyao, et al., Capsule Polishing Device and Method for Capsule Polishing, U.S. Appl. No. 12/777,820, filed May 11, 2010, 26 pages.

Sussman, Glenn, et al., Small Gauge Ablation Probe for Glaucoma Surgery, U.S. Appl. No. 12/707,747, filed Feb. 18, 2010, 11 pages.

Lewandowski, Julia T., "Improving Ab Interno Trabeculotomy, A combination of advanced technology and insightful design may prompt surgeons to adopt a new technique for lowering IOP," article, Jul. 2007, 4 pages, Bryn Mawr Communications.

Karmel, Miriam, "Glaucoma Surgies: Trabectome and Canaloplasty Take the Stage," publication, May 2009, pp. 29-30, American Academy of Ophthalmology.

Abstract of SU1805938; Publication date Mar. 30, 1993; Priority date Mar. 11, 1991.

Fowler, Daniel Wayne, Office Action Summary, U.S. Appl. No. 12/707,747, Aug. 31, 2012, 34 pages.

Holloway, Ian Knobel, Office Action Summary, U.S. Appl. No. 12/249,982, Jan. 3, 2014, 9 pages.

Abstract of JP4834337(B2); Publication date Dec. 14, 2011.

Giuliani, Thomas Anthony, Office Action Summary, U.S. Appl. No. 12/777,820, Jun. 6, 2013, 40 pages.

* cited by examiner

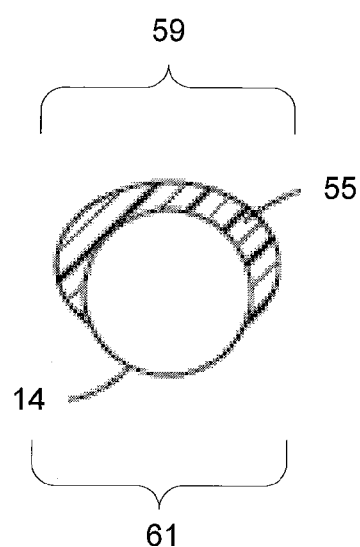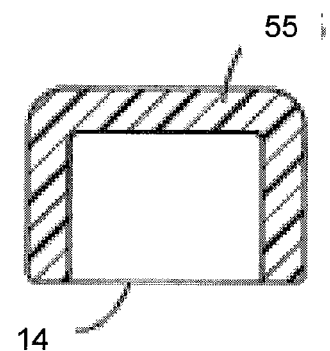
*FIG. 6a*  *FIG. 6b*

CAPSULOTOMY REPAIR DEVICE AND METHOD FOR CAPSULOTOMY REPAIR

PRIORITY CLAIM

This application is a continuation-in-part application of U.S. patent application Ser. No. 12/477,175 titled "Capsularhexis Device With Flexible Heating Element Having an Angled Transitional Neck" which was filed Jun. 3, 2009 whose inventors are Guangyao Jia and Glenn R. Sussman which is hereby incorporated by reference in its entirety as though fully and completely set forth herein.

FIELD OF THE INVENTION

The present invention relates generally to the field of ophthalmic surgery and more particularly to methods and apparatus for performing a capsularhexis.

DESCRIPTION OF THE RELATED ART

An accepted treatment for the treatment of cataracts is surgical removal of the lens (e.g., through phacoemulsification) and replacement of the lens function by an artificial intraocular lens (IOL). Prior to removing the cataractous lens, an opening, or rhexis, may be made in the anterior capsule. During phacoemulsification, there may be tension on the cut edges of the anterior capsularhexis while the lens nucleus is emulsified. Further, if the capsule is opened with numerous small capsular tears, the small tags that remain may lead to radial capsular tears that may extend into the posterior capsule. Such a radial tear may constitute a complication since it may destabilize the lens for further cataract removal and safe intraocular lens placement within the lens capsule later in the operation. In addition, if the posterior capsule is punctured then the vitreous may gain access to the anterior chamber of the eye. If this happens, the vitreous may need to be removed by an additional procedure with special instruments. The loss of vitreous may lead to subsequent retinal detachment and/or infection within the eye. Further, while some ophthalmic procedures may also require a posterior capsularhexis, current devices designed for anterior capsularhexis may not have an optimal geometry for performing a posterior capsularhexis.

SUMMARY OF THE INVENTION

Various embodiments of a capsulotomy repair device include a resistive-heating element comprising an electrically resistive, superelastic wire forming a loop between first and second ends of the superelastic wire. The first and second ends of the loop may at least partially extend at an angle from a planar face defined by the loop, to an insulating portion, to form a transitional neck between the loop and the insulating portion. The capsulotomy repair device may be positioned in the eye relative to a capsularhexis perimeter. For example, the capsulotomy repair device may overlap tears in the capsularhexis perimeter and remove the tear by burning around the tear (thus forming an adjusted capsularhexis perimeter). The capsulotomy repair device may include an oblong/elliptical shape. Different shaped wires may also be used for different tear geometries (for example, circular and parabolic). Different sized loops may also be used to accommodate different tear sizes. In some embodiments, the transitional neck may have a gap between the first and second ends at the insulating portion that is wider than a gap between the first and second ends on the opposing side of the transitional neck. The gap in the loop of superelastic wire may be sufficiently small to allow the loop to form a continuous cut in a capsule of an eye.

BRIEF DESCRIPTION OF THE DRAWINGS

For a more complete understanding of the present invention, reference is made to the following description taken in conjunction with the accompanying drawings in which:

FIGS. 6a-b illustrate alternate configurations of the wire used in the capsularhexis device, according to various embodiments;

It is to be understood that both the foregoing general description and the following detailed description are exemplary and explanatory only and are intended to provide a further explanation of the present invention as claimed.

DETAILED DESCRIPTION OF THE EMBODIMENTS

Incorporation by Reference

U.S. Patent Application Publication entitled "CAPSULARHEXIS DEVICE," Publication No. 20060100617, Ser. No. 10/984,383, by Mikhail Boukhny filed Nov. 9, 2004 is hereby incorporated by reference in its entirety as though fully and completely set forth herein.

U.S. patent application entitled "CAPSULARHEXIS DEVICE WITH FLEXIBLE HEATING ELEMENT," Ser. No. 12/249,982, by Glenn Sussman and Guangyao Jia filed Oct. 13, 2008 is hereby incorporated by reference in its entirety as though fully and completely set forth herein.

Figure 1A:
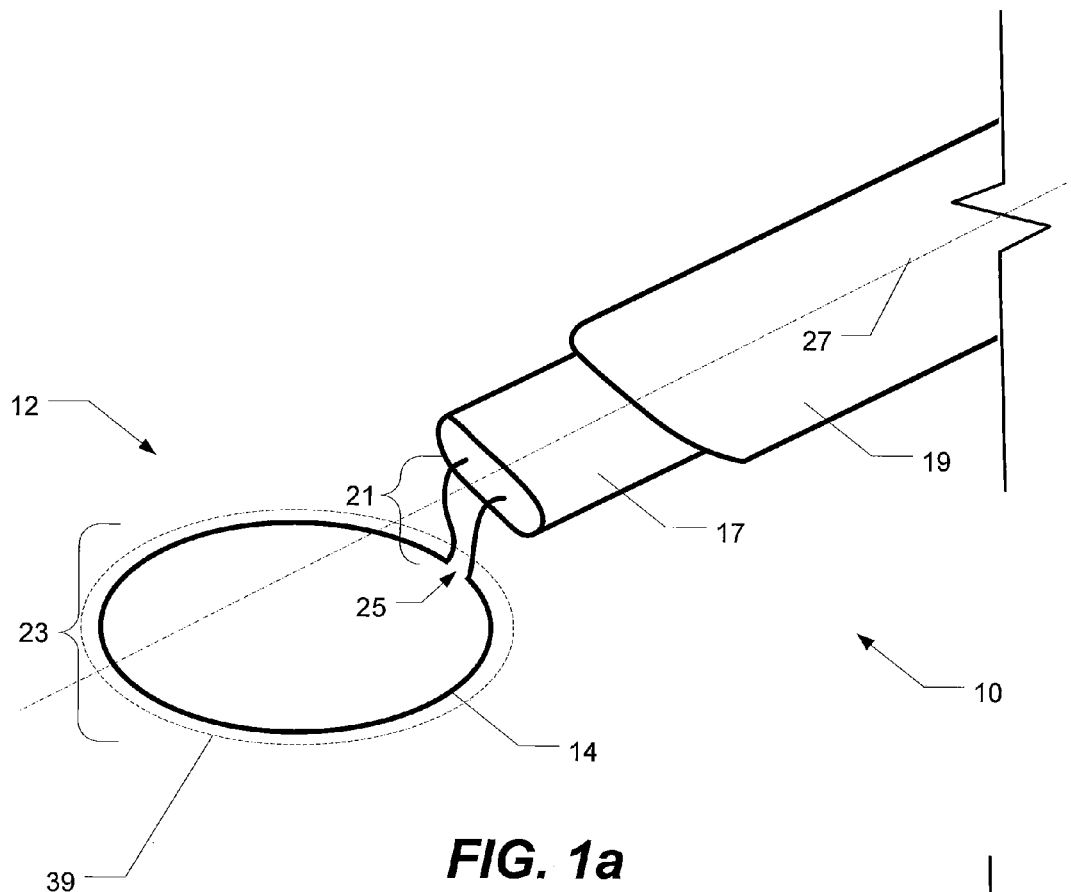
FIGS. 1a-b illustrate various positions of a capsularhexis device, according to an embodiment.
Figure 1B:
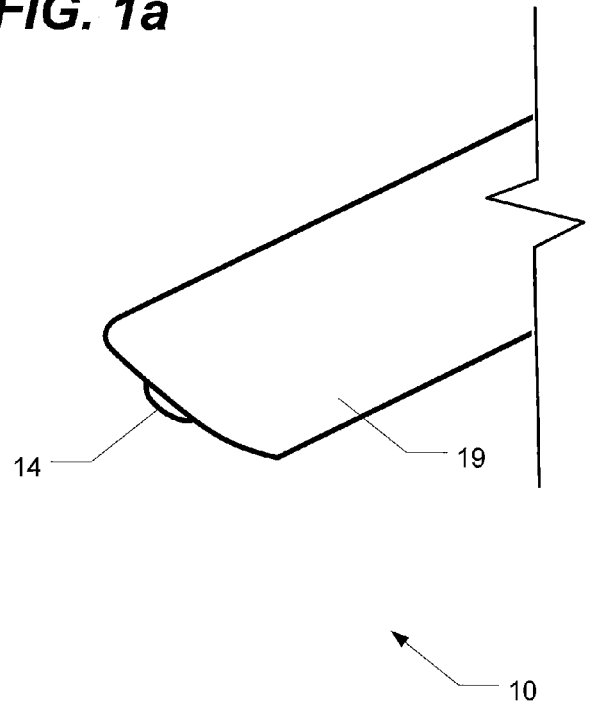

FIGS. 1a-b show a plan view of some embodiments of a capsularhexis device 10. Those skilled in the art will appreciate that FIGS. 1a-b, like the several other attached figures, are not to scale, and that several of the features may be exaggerated to more clearly illustrate various features. Those skilled in the art will also appreciate that the illustrated structures are only exemplary, and not limiting. In some embodiments, the capsularhexis device 10 may include a substantially circular, flexible loop 23 of a resistance-heating element 12 that may be energized to produce localized heating on an anterior lens capsule 509 and/or posterior lens capsule 513 (e.g., see FIG. 5) of an eye 32 to create a through cut or define a weakened boundary for detachment of the portion of the capsule 36 within the loop 23. The capsularhexis device 10 may be positioned within the anterior chamber 34 through a small incision 505 to perform the capsularhexis, or capsulotomy. This procedure may facilitate, for example, phacoemulsification of a cataractous lens and insertion of an artificial intraocular lens (IOL).

Figure 4:
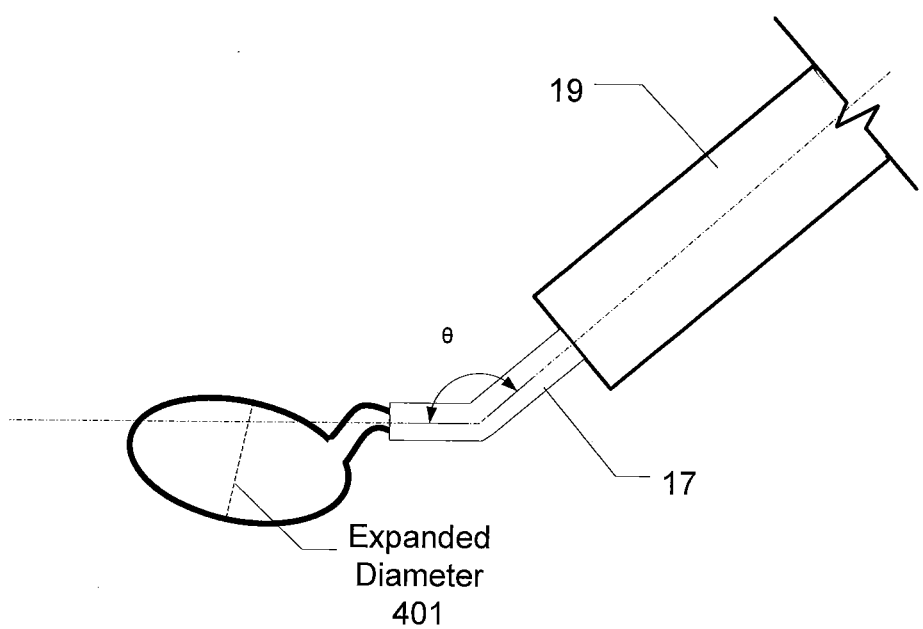
FIG. 4 illustrates an angled capsularhexis device, according to an embodiment.
Figure 5:
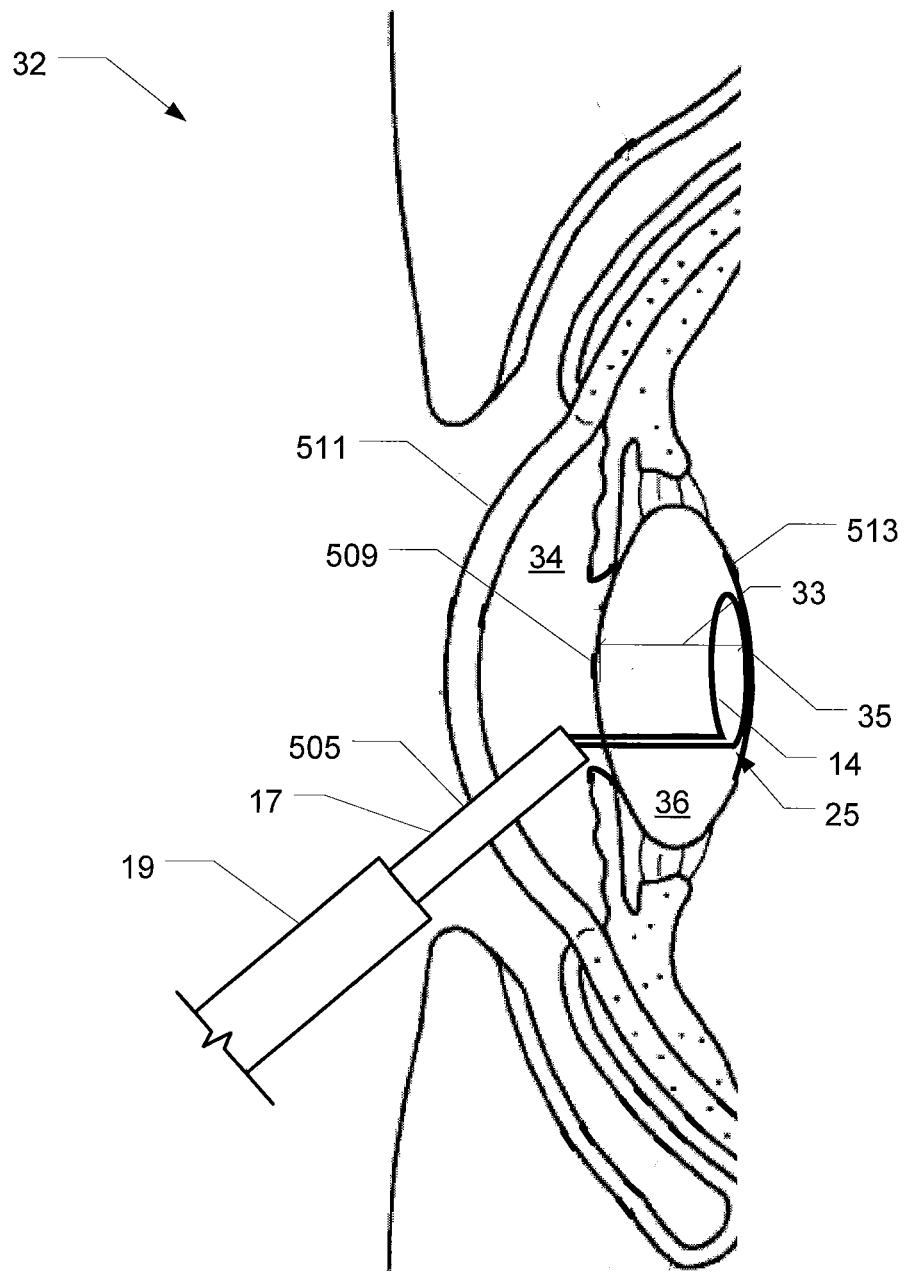
FIG. 5 illustrates a side view of the capsularhexis device inserted into the posterior capsule, according to an embodiment.

As seen in FIGS. 1a-d, in various embodiments, the heating element 12 may include a transitional neck 21 (e.g., formed by first and second wire ends 31a-b or 31c-d (referred to generally herein as wire ends 31)) with an offsetting bend so as to offset a planar face 39 of the loop 23 above or below a centerline 27 of an insertion sleeve 19. The wire ends 31 forming transitional neck 21 may bend away from the centerline 27 (e.g., a distance 29 as shown in FIG. 1e). Bending away from the centerline 27 may allow the loop 23 to be placed more parallel with an anterior and/or posterior capsule face. As seen in FIG. 5, the wire ends 31 in the transitional neck 21 may displace the loop 23 a depth 33 of the capsule 36 to position the loop 23 for uniform contact with the posterior capsule face 35. Since the heat-affected zone of the wire 14 is smaller on the capsule because of the perpendicular orientation with respect to the capsule surface, thermal insulation may not be needed for prevention of collateral thermal damage to the capsule region underneath. In some embodiments, the diameter 401 (e.g., see FIG. 4) of the loop 23 may be adjusted according to whether the loop 23 will be used in anterior capsulorhexis or posterior capsulorhexis (which may use a smaller diameter 401 (e.g., approximately in a range of 2-4 millimeters (mm)) than in anterior capsulorhexis which may use a diameter approximately in a range of 4-6 mm). Other diameters are also contemplated. In some embodiments, the transitional neck 21 may have a length (a distance from the insulating portion 17 to the loop 23) of approximately 1-2 mm (other lengths are also contemplated).

Figure 1C:
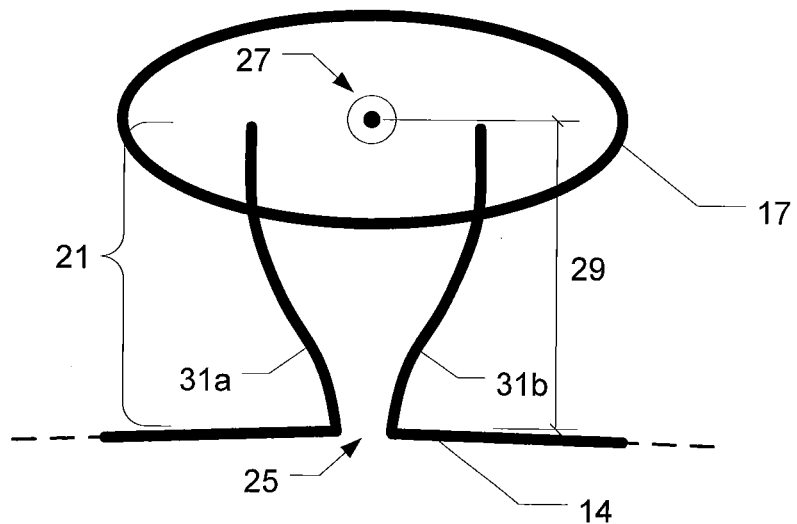
FIGS. 1c-d illustrate a head-on, cross-sectional view of two embodiments of a transitional neck for a capsularhexis device.
Figure 1D:
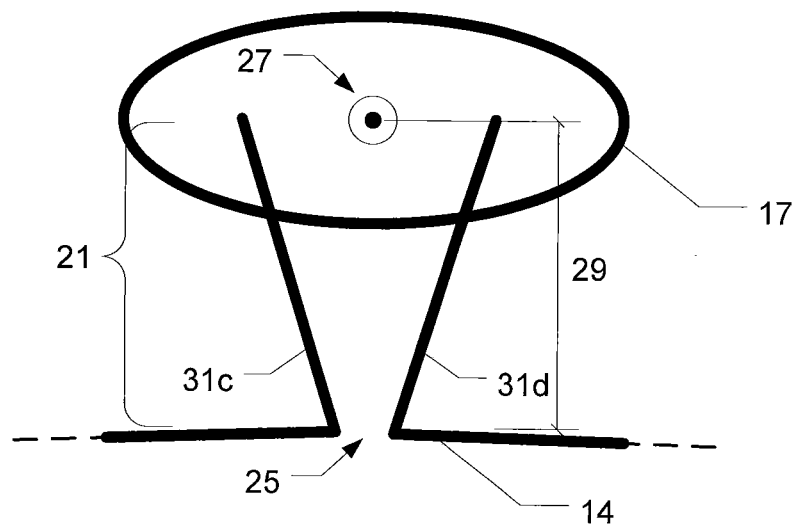
Figure 1E:
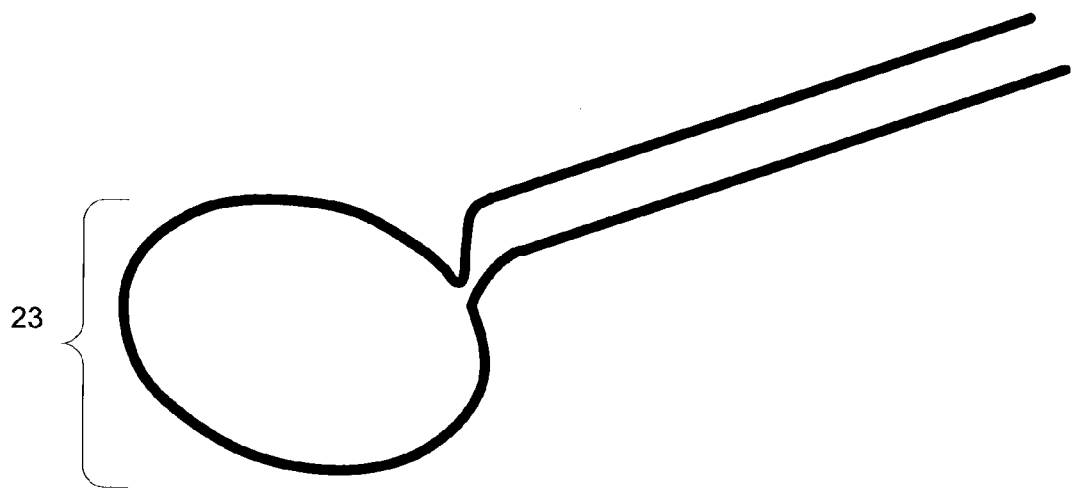
FIGS. 1e-f illustrate an embodiment of the loop for posterior capsulorhexis.
Figure 1F:
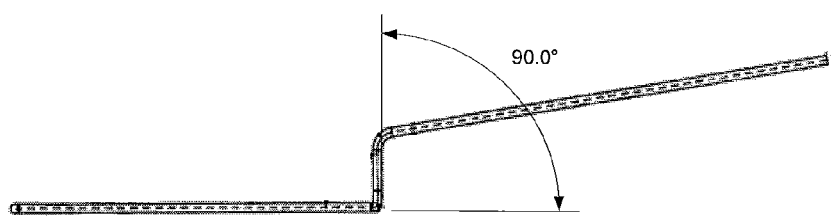
Figure 1G:
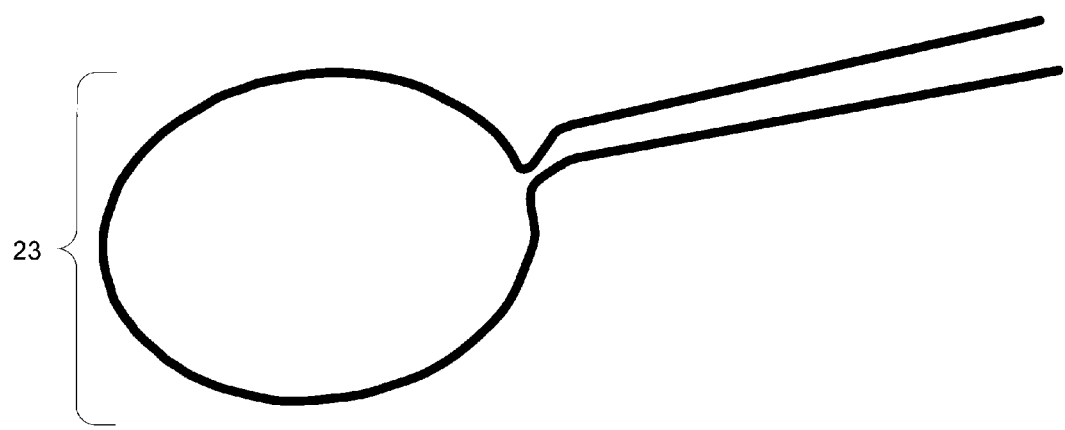
FIGS. 1g-h illustrate an embodiment of the loop for anterior capsulorhexis.
Figure 1H:
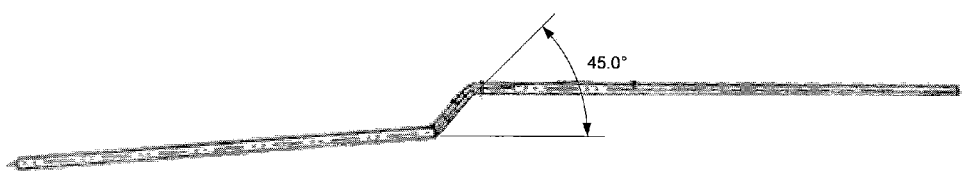

In some embodiments, the transitional neck 21 may be substantially (e.g., +/−20 degrees) perpendicular to a planer face 39 of the loop 23 (e.g., for posterior capsulorhexis as seen in FIGS. 1e-f). Other angles are also contemplated. For example, the transitional neck 21 may be approximately 135 degrees (e.g., for anterior capsulorhexis as seen in FIGS. 1g-h) or 45 degrees measured to a back side of the plane as seen in FIG. 1h. Other angles are also contemplated (e.g., the transitional neck may be approximately in a range of 30 degrees to 90 degrees from a back side of the plane). In some embodiments, the wire ends 31 may be bent toward each other to reduce the size of gap 25 between the wire ends 31 of the resistance-heating element 12. The gap 25 may be minimized to maintain enough distance to prevent a short between ends of the gap (i.e., so current travels around the loop 23). For example, the gap 25 may have a width of approximately 0.003 inches plus or minus 0.001 inches. Other dimensions are also contemplated (e.g., 0.006 inches or, as another example, smaller than 0.002 inches). The gap 25 may insulate the wire ends 31 from each other (such that electric current travels through wire 14 and not across gap 25). Bending away from the centerline 27 may allow a further reduction in the size of gap 25 than would be otherwise possible if the wire ends 31 were parallel to the centerline 27. The reduced gap size may result in a more complete circular through cut or a boundary for detachment. (While a circular loop 23 is shown, other shapes are also contemplated (e.g., elliptical, rectangular, etc)). Due to the reduced gap size, contact with the capsule 36 and wire 14 around gap 25 may provide bipolar diathermy in the capsule 36 to facilitate a more complete capsulotomy despite the discontinuity (i.e., gap 25) on the heating element 12. The angled orientation of the transitional neck 21 with respect to the planar face 39 may reduce straight edges in the capsule 36 at the gap 25 to form a more circular ring with complete (or mostly complete) rhexis. Neighboring heat from the wire 14 on either side of the gap 25 may thermally cut the portion of the capsule 36 between the gap 25 because of the reduced width of gap 25.

Wire ends 31 may be curved and/or straight (see FIGS. 1c-d). Other configurations for the wire ends 31 are also contemplated. While the term "bending" is used throughout, the wire ends 31a-b may be formed and/or shaped using other methods (e.g., mold casting, extrusion, etc).

In various embodiments, the geometry of the loop 23 may be adjusted based on whether the loop 23 will be used for posterior capsulorhexis (e.g., see FIGS. 1e-f) or anterior capsulorhexis (e.g., see FIGS. 1g-h).

According to several embodiments, the resistive-heating element 12 may include an at least partially bare resistance-heating element made from a super-elastic wire. By combining the super-elasticity of the wire material with a relatively high electric resistivity, a collapsible, ring-shaped heating element 12 may be constructed to perform capsulotomy by localized heating. Because the heating element 12 may be collapsible, the heating element 12 may be easily inserted into the eye 32 through a small incision 505 (e.g., 2 mm) in the cornea 511. Other incision sizes and locations are also contemplated.

The capsularhexis device 10 may include a fine, superelastic wire 14 for the heating element 12. In some embodiments, the wire 14 may be formed from a nickel titanium alloy, such as Nitinol, which may exhibit superelastic and shape memory properties. Because the wire 14 may be superelastic (which term is intended herein as a synonym for the somewhat more technically precise term "pseudoelastic"), the wire 14 may be able to withstand a significant amount of deformation when a load is applied and return to its original shape when the load is removed. (Those skilled in the art will appreciate that this property is distinct from, although related to, "shape memory", which refers to a property exhibited by some materials in which an object that is deformed while below the material's transformation temperature returns to its former shape when warmed to above the transformation temperature. Nitinol exhibits both properties; superelasticity is exhibited above the transformation temperature.) Further, Nitinol is resistive, and can thus be heated with an electrical current, making it useful for forming the resistive-heating element 12 illustrated in FIGS. 1a-c. Of course, those skilled in the art will appreciate that other materials that are resistive and superelastic may be used instead of Nitinol in some embodiments.

Because the wire 14 has superelastic properties, the wire may be able to collapse during insertion and return to a pre-formed shape during use. In some embodiments, a viscoelastic agent may be used to inflate the anterior chamber 34 prior to the capsulotomy. The viscoelastic agent may have a sufficiently low thermal diffusivity to serve as a thermal insulator around the heating element 12, thus facilitating the formation of a highly concentrated thermally affected zone in the immediate vicinity of the heating element 12. The concentration of this zone may reduce collateral damage to nearby tissue. Although in practice it may be unavoidable to trap a thin film of viscoelastic material between the heating element and the capsule, a small defined area on the capsule 36 may still respond sufficiently fast to the temperature rise in the heating element to avoid collateral damage, due to the small thickness (e.g., approximately 10 micrometers) of the fluid film.

The resistive-heating element 12 may include a loop 23 formed from the superelastic wire 14. The ends of the wire 14, extending away from the loop 23 to form a lead section, may be kept electrically separate with a flexible, electrically insulating portion 17. In some embodiments, the insulating portion 17 may surround a portion of the lead section. However, those skilled in the art will appreciate that insulating portion 17 may surround only one lead, or may only partially surround either or both leads, in some embodiments, provided that the two leads extending away from the loop 23 and into the insertion sleeve 19 may be kept electrically separate so that electrical current may be passed through the loop of the resistive-heating element 12. Insulating portion 17 may include a bio-compatible and high temperature-resistant material, such as polyimide or Teflon™. In some embodiments, insulating portion 17 may be flexible. In some embodiments, one or more crimp tubes (e.g., silver crimp tubes) may be used to receive the loop 23 (the tubes may be crimped onto the loop 23 to secure the loop 23 into the handpiece). In some embodiments, insulating portion 17 may extend over the crimp tubes to electrically insulate the tubes from each other.

In some embodiments, insertion sleeve 19 may include a flat or cylindrical tube that engages a portion of a lead section, including the insulating portion 17. In some embodiments, the insertion sleeve 19 may form a slip-fit with the insulating portion 17. Insertion sleeve 19 may be used to insert the heating element 12 into the eye 32 during the capsularhexis procedure and to retract the heating element 12 afterwards. The insertion sleeve 19, which may be made from a thermoplastic, may also contain electrical connectors and/or connecting wires so that the heating element 12 may be selectively connected to a power source for heating. In some embodiments, the insertion sleeve 19, insulation material 17, and wire 14 may form a disposable unit that can be selectively connected during use to a handpiece or other apparatus that can supply electrical current. In some embodiments, insertion sleeve 19 may be coupled to handpiece 41 (e.g., see FIGS. 2a-b) which may be coupled to a surgical console 43 (e.g., see FIG. 8).

Figure 2A:
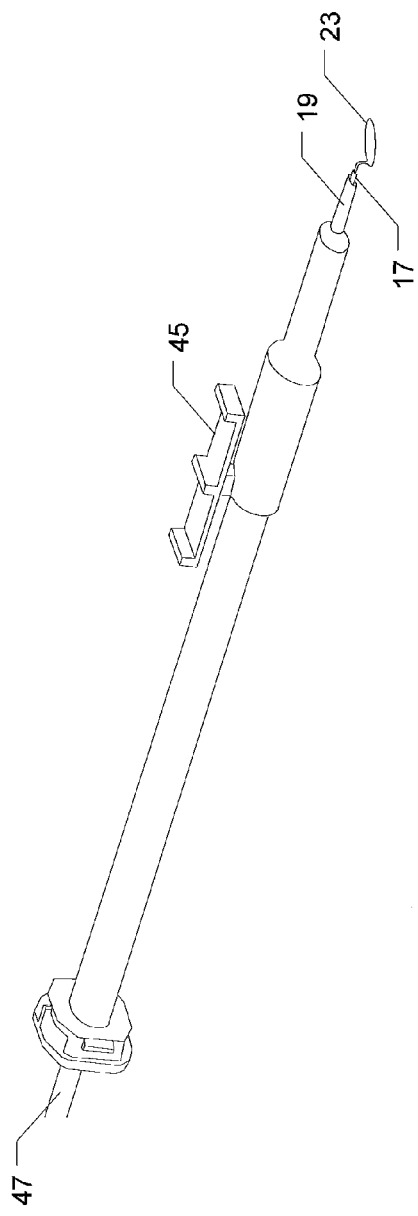
FIGS. 2a-b illustrate an embodiment of the handpiece.
Figure 2B:
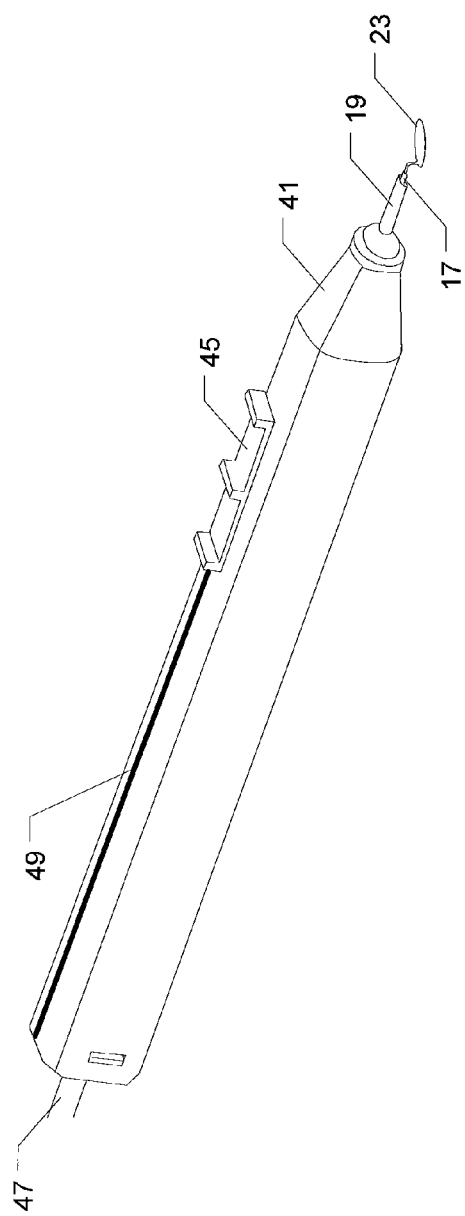
Figure 2C:
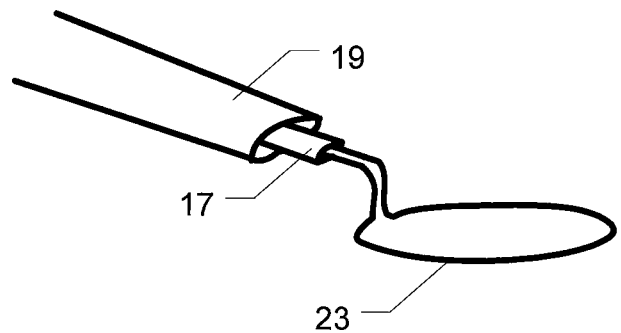
FIGS. 2c-d illustrate an embodiment of an exposed loop and a withdrawn loop.
Figure 2D:
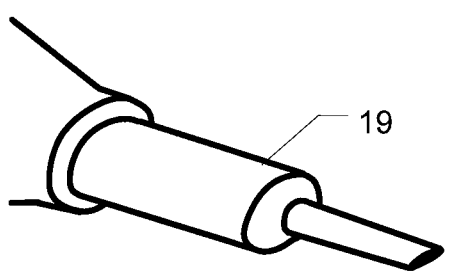

Because of its superelastic properties, the heating element 12 may be collapsed for insertion into the anterior chamber 34 of the eye 32, regaining its pre-defined shape within the anterior chamber 34. Accordingly, some embodiments include or may be used with an insertion sleeve 19 through which the heating element 12 is pushed. A collapsed heating element 12 in a retracted position in the insertion sleeve 19 is shown in FIG. 1b and FIG. 2d. The heating element 12 may be collapsible upon retracting the heating element 12 into the insertion sleeve 19 and expandable to its original shape upon ejection from the insertion sleeve 19. In some embodiments, the insertion sleeve 19 and insulating portion 17 may be incorporated in a single device (or separate devices). In some embodiments, a separate cartridge may be used to collapse/expand the loop 23 through (e.g., separate from and/or in place of insertion sleeve 19). As seen in FIGS. 2a-b, a handpiece 41 may include a retraction lever 45 which may ride in a slot 49. When retraction lever 45 (attached to the insertion sleeve) is pushed towards the end of the slot 49, the loop 23 may be enclosed in the insertion sleeve 19 (e.g., see FIG. 2d). When the retraction lever 45 is pulled back along the slot 49, the loop 23 may exit the insertion sleeve 19 (see FIG. 2c). Other configurations of the handpiece are also contemplated. In various embodiments, the loop 23 may be partially withdrawn into the insertion sleeve 19 (e.g., as seen in FIG. 1b) or fully withdrawn into the insertion sleeve 19 (e.g., as seen in FIG. 2d) before and/or after the procedure. In some embodiments, the partially exposed wire (as seen in FIG. 1b) may act as a guide as the insertion sleeve 19 is inserted into an incision.

Figure 3A:
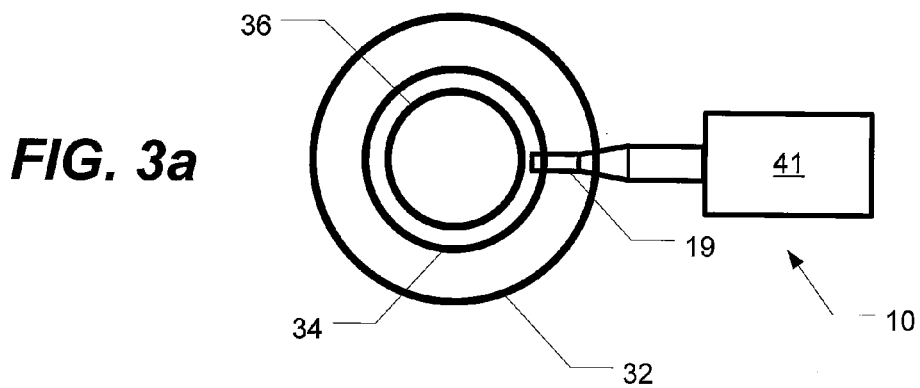
FIGS. 3a-d illustrate expansion and retraction of the capsularhexis device through an insertion sleeve, according to an embodiment.

FIGS. 3a-d illustrate the insertion of the heating element 12 into an eye 32, according to an embodiment. Prior to the procedure, the loop 23 of the heating element 12 may be withdrawn into the insertion sleeve 19, so that, as seen in FIG. 3a, the loop 23 of heating element 12 is contained almost entirely within the insertion sleeve 19. Thus, the leading tip of the apparatus may be inserted into the anterior chamber 34 of the eye 32, as shown in FIG. 3a, through a small incision 505 (see FIG. 5).

Figure 3B:
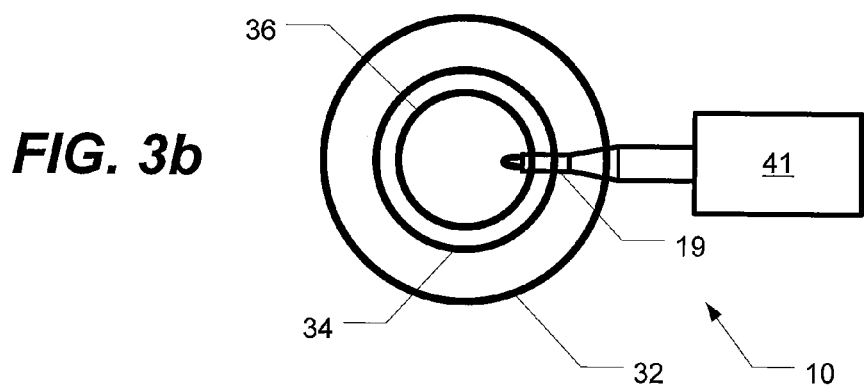
Figure 3C:
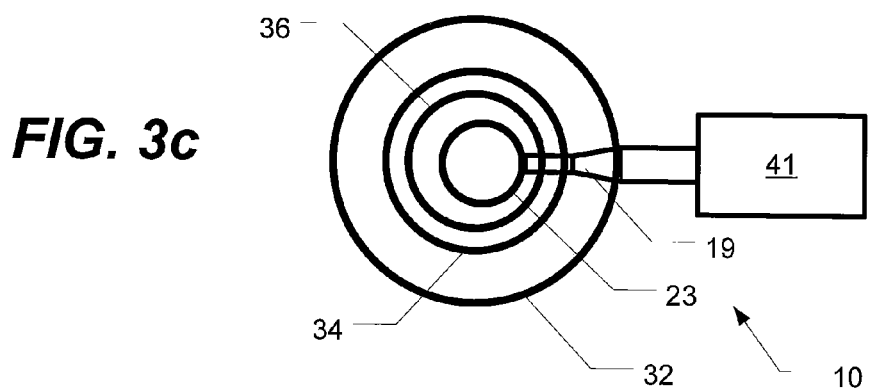
Figure 3D:
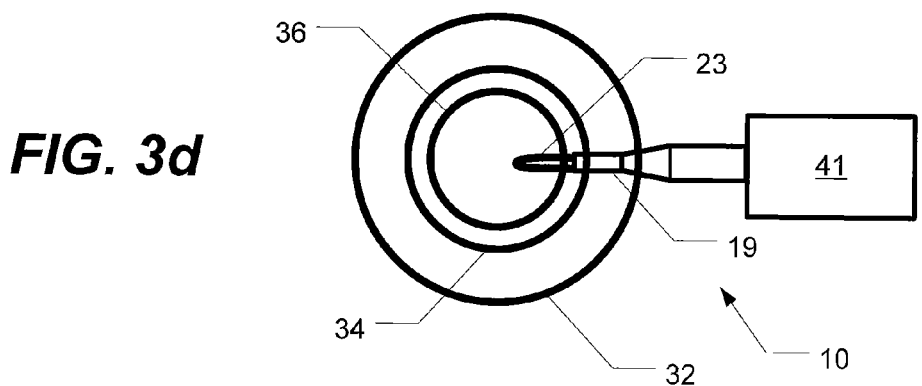

As shown in FIG. 3b, the insertion sleeve 19 and collapsed heating element 12 may be pushed inside the lens capsule 36 (for posterior capsulotomy) (or near the anterior lens capsule for anterior capsulotomy). The loop 23 of the heating element 12 may then regain its pre-determined shape, as shown in FIG. 3c, and may then be positioned against the capsule 36. The transitional neck may not be perceptible from the top down perspective of the capsularhexis devices in FIGS. 3a-d. The heating element 12 may then be energized, e.g., with a short pulse or series of pulses of current. As discussed above, this heating may sear capsule 36 (e.g., the anterior lens capsule 509 and/or posterior lens capsule 513) to create a smooth continuous cut on the capsule 36. The heating element 12 may then be retracted into the insertion sleeve 19, as shown in FIG. 3d, and then removed from the eye 32. The cut portion of the capsule 36 may be readily removed using a conventional surgical instrument, such as forceps.

Because the superelastic wire 14 is flexible, the insertion sleeve 19 may be bent upwards when the heating element 12 is placed against the capsule 36. Because the deformation properties of the wire 14 (and, in some cases, the insulation 17) may be determined for a given device 10, the bending angle formed with respect to the plane of the heating element 12 may be used as an indication of the force applied to the capsule 36 by the heating element 12. Thus, a range of acceptable bending angles may be defined for a particular device 10, to correspond to a range of desirable application forces for optimal cauterization of the capsule 36. Accordingly, a surgeon may conveniently achieve a desired contact force between the heating element 12 and the capsule 36 by simply manipulating the bending angle to match or approximately match a pre-determined angle θ, as shown in FIG. 4. In some embodiments, angle θ may be defined as the angle between a plane of the loop 23 and the insulating portion 17 (which may be straight relative to the heating element 12 of the loop 23). For example, the angle θ may be characterized by the bend in the transitions between the loop 23 and the neck 21.

In some embodiments, to further reduce any potential collateral damage to tissue near the heating element 12, a thermally insulating layer may be disposed on at least a top face 59 of the loop 23 formed by the resistive-heating element 12, such that a bottom face 61, which may be disposed against the capsule 36 during the capsularhexis procedure, may be left bare. A cross-sectional view of one such embodiment is shown in FIG. 6A, which shows a cross-section of a round wire 14, partially surrounded with a thermally insulating layer 55. In some embodiments, the superelastic wire 14 may have a square or rectangular cross-section, as shown in FIG. 6B, in which case insulation 55 may be disposed on three sides of the wire 14. In either case, insulation 55 may be disposed on the wire 14 around all or substantially all of the loop 23 of the resistive-heating element 12.

Figure 7:
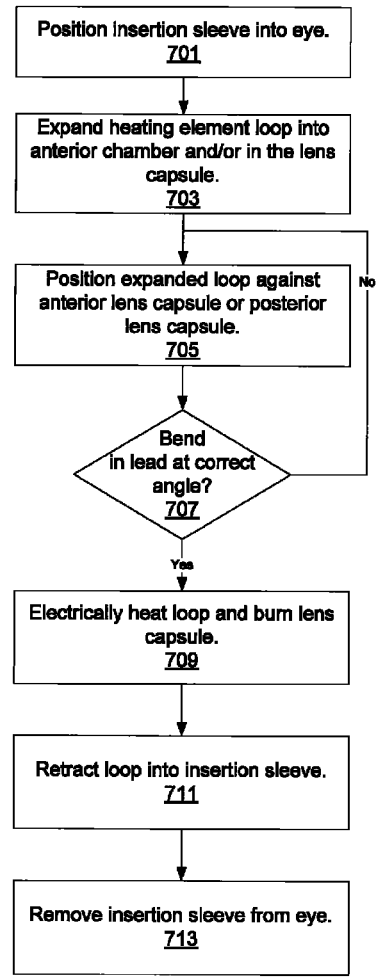
FIG. 7 illustrates a flowchart of a method for performing a capsulotomy, according to an embodiment.

With the above-described device configurations in mind, those skilled in the art will appreciate that FIG. 7 illustrates a method for utilizing a capsularhexis device according to some embodiments. The elements provided in the flowchart are illustrative only. Various provided elements may be omitted, additional elements may be added, and/or various elements may be performed in a different order than provided below.

At 701, the insertion sleeve 19 may be positioned into the eye 32. The heating element 12 may be retracted into the insertion sleeve 19 prior to insertion into the eye. For example, the heating element 12 may be retracted by a surgeon and/or during manufacturing of the device 10. FIG. 1*b* illustrates an embodiment of a retracted heating element 12. In some embodiments, positioning the insertion sleeve 19 into the eye may include making a small incision 505 in the cornea 511 (or other part of the eye 32) for inserting the insertion sleeve 19.

At 703, the heating element loop 23 may be expanded into the anterior chamber 34 of the eye 32 (for anterior capsulorhexis) or in the lens capsule (for posterior capsulorhexis). Because the heating element 12 described herein may be collapsed, the insertion sleeve 19 may be dimensioned to fit through an incision 505 that is smaller than the expanded diameter 401 of the heating element's loop 23.

At 705, once the loop 23 of the heating element 12 is expanded into the eye 32, it may be positioned against the anterior lens capsule 509 and/or the posterior lens capsule 513. In some embodiments, the applied force between the heating element 12 and the capsule 36 may be gauged by assessing a bend in the lead section of the heating element 12.

At 707, the angle between the insertion sleeve 19 and the plane formed by the heating element 12 may be matched to a pre-determined angle (e.g., see FIG. 4) to determine if the correct force is applied.

At 709, after the heating element 12 is positioned against the capsule 36, the heating element 12 may be energized by the application of electrical current, so that the loop 23 may be heated to "burn" the lens capsule 36 with a substantially circular, continuous cut on the anterior lens capsule 509 and/or the posterior lens capsule 513.

At 711, once the burning of the capsule 36 is complete, the heating element 12 may be retracted into the insertion sleeve 19 and, at 713, the insertion sleeve 19 may be removed from the eye 32. In some embodiments, the detached portion of the capsule may be removed using a surgical instrument such as forceps.

As was briefly discussed above, the energizing of the resistance-heating element 12 may advantageously include a short pulse (e.g., 20 milliseconds) of electrical current, or a series of pulses (e.g., 1 millisecond each). In some embodiments, pulsed radio-frequency power may be used to reduce collateral thermal damage on the capsule and avoid electrochemical reaction at the gap 25. The frequency, waveform, voltage, pulse width, and duration of the radiofrequency power may be configured to attain a continuous through-cut on the capsule 36 while reducing collateral damage. Those skilled in the art will appreciate that the power settings (e.g., voltage, current, pulse width, number of pulses, etc.) may be established for a particular heating element configuration so that a continuous, circular (or oval) through-cut on the capsule 36 may be attained, while minimizing collateral damage to portions of the capsule 36 surrounding the portion to be removed. When determining the power settings for a particular heating element 12 according to those described herein, those skilled in the art may consider that multiple working mechanisms may contribute to the "cutting" of the capsule 36. For instance, a steam "explosion" in the viscoelastic material and tissue water caused by rapid heating of the heating element 12 may contribute to the cut-through of the capsule 36, in addition to the thermal breakdown of the capsule material.

Figure 9:
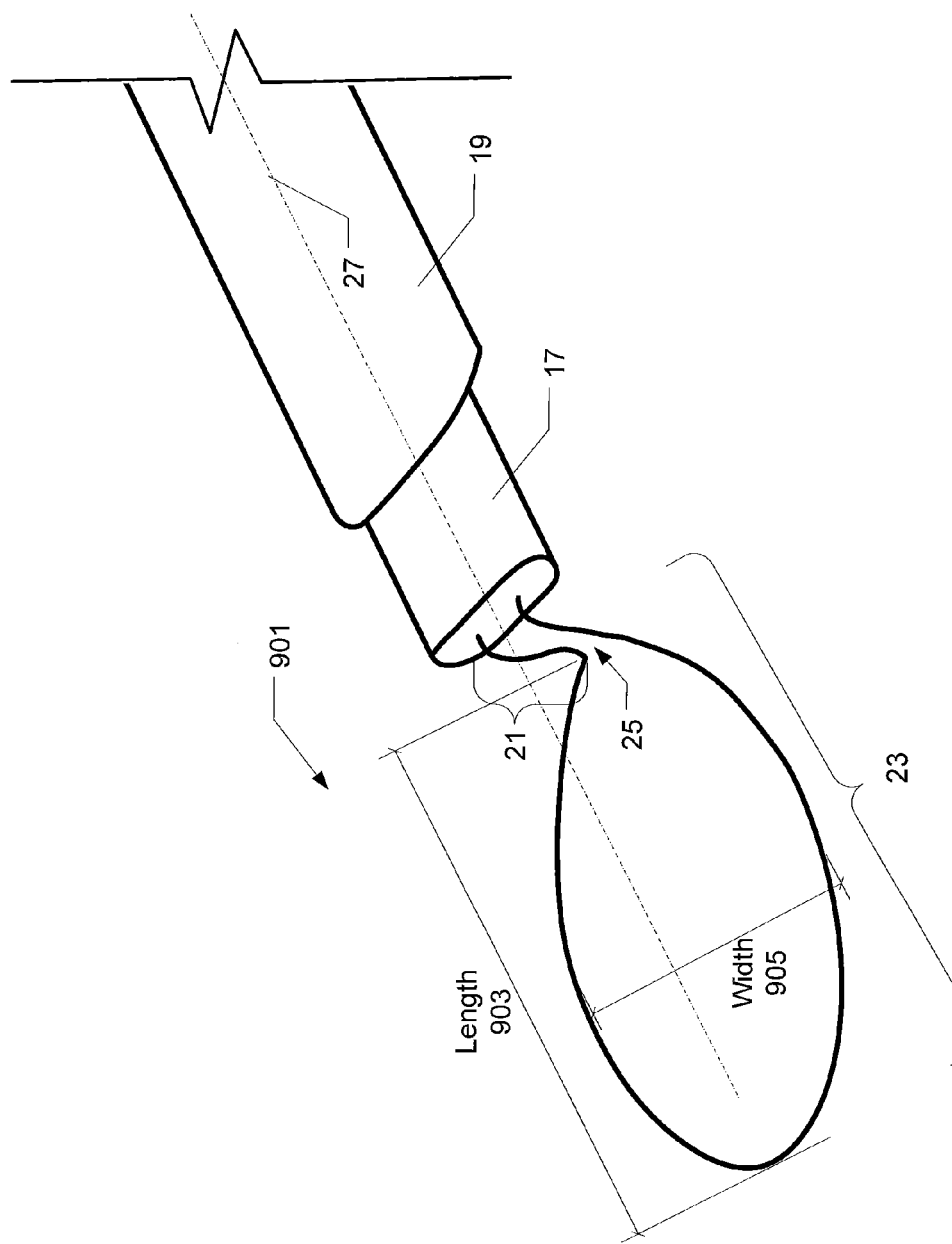
FIG. 9 illustrates a capsulotomy repair device, according to an embodiment.

FIG. 9 illustrates an embodiment of a capsulotomy repair device. In some embodiments, a smaller capsularhexis device 10 (herein referred to as "capsulotomy repair device 901") may be used to repair capsulotomies (e.g., a continuous curvilinear capsulorhexis (CCC)). During a capsulotomy, rips or tears may occur along the edges of the capsulotomy perimeter 1041 that may extend into the posterior capsule. These radial tears may destabilize the lens for further cataract removal and safe intraocular lens placement. The resistive-heating element loop 23 of the capsulotomy repair device 901 may have an oblong shape and may have a length and width that is smaller than a length and width of a lens capsule. In some embodiments, both the length and width may be smaller than approximately 10 millimeters (mm) (e.g., a length approximately in a range of 4 to 5 mm and a width approximately in a range of 2 to 3 mm). Other lengths and widths are also possible. In some embodiments, the loop 23 of the capsulotomy repair device 901 may have a length and width that is smaller than a capsulotomy perimeter 1041 (e.g., as seen in FIGS. 3*a-d*, a capsulotomy perimeter 1041 may be shaped to remove the lens capsule for subsequent intraocular lens placement within the lens capsule). While an oblong/elliptical shape is shown in FIGS. 9-11*b*, other shapes may also be used. For example, different shaped wires may be used for different tear geometries. Wire shapes may include, for example, circular and parabolic. Different sized loops and length to width ratios may also be used to accommodate different tear sizes.

In some embodiments, the capsulotomy repair device 901 may have a structure that is substantially similar to the capsularhexis device 10 described above (but, in some embodiments, may have smaller dimensions than the capsularhexis device 10). For example, the loop 23 of the capsulotomy repair device 901 may include a heating element with a transitional neck 21 (e.g., see FIG. 1*a*) with an offsetting bend so as to offset a planar face 39 of the loop 23 above or below a centerline 27 of an insertion sleeve 19 (the wire ends 31 forming transitional neck 21 may bend away from the centerline 27). In some embodiments, the capsulotomy repair device 901 may not include a transitional neck (e.g., the capsulotomy repair device 901 may include a straight neck). In some embodiments, the capsulotomy repair device 901 may use separate crimp tubes around each end of the loop 23 to insulate the ends from each other in the insertion sleeve 19. In some embodiments, the insertion sleeve 19 may not be used. For example, the loop 23 may have a reduced diameter that can be inserted into the eye without being retracted into an insertion sleeve 19.

Figure 10B:
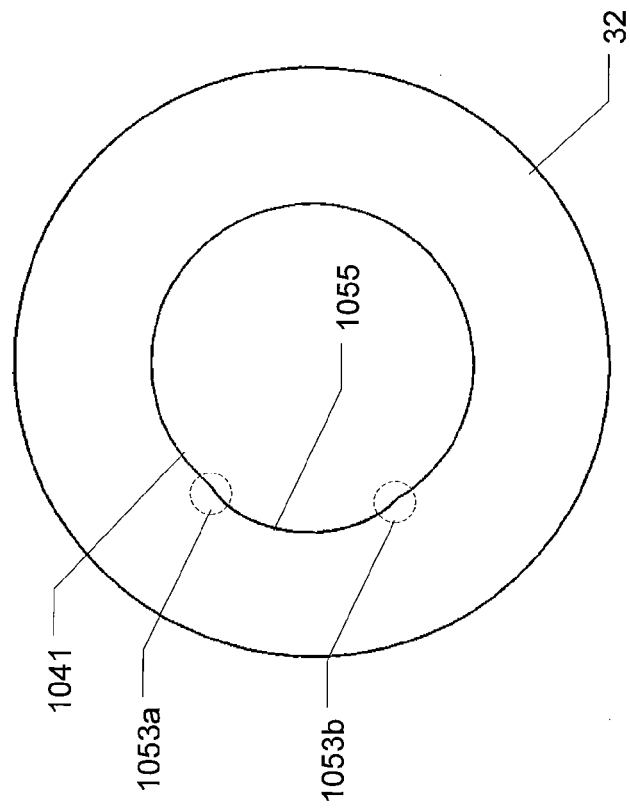
FIGS. 10a-b illustrate a small tear repair using the capsulotomy repair device, according to an embodiment.
Figure 10A:
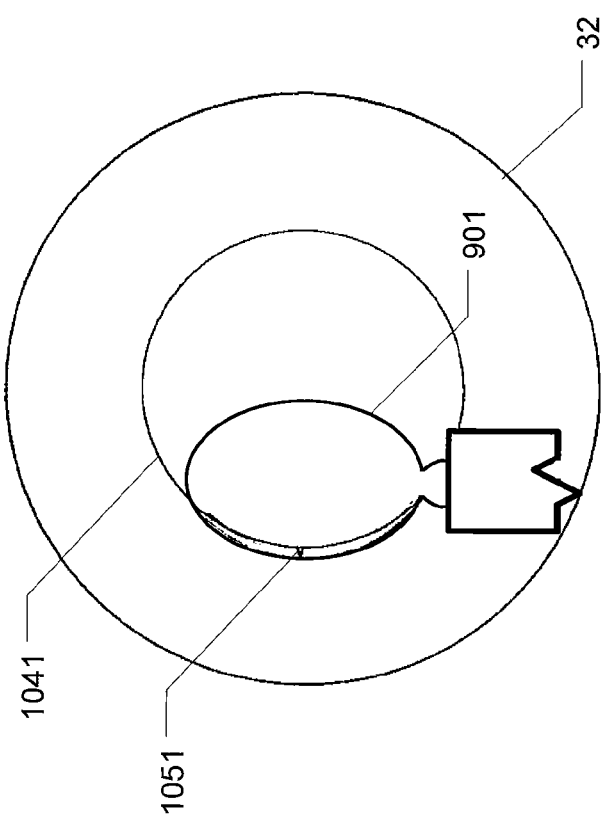

FIGS. 10*a-b* illustrate an embodiment of a small tear repair using the capsulotomy repair device. As noted above, the loop 23 may be retracted into an insertion sleeve 19 prior to insertion into the eye. Once in the eye, the loop 23 of the capsulotomy repair device 901 may be extended out of the sleeve 19 where it may expand to its original shape. As seen in FIG. 10*a*, the loop 23 may be aligned to overlap with a small side tear 1051 (e.g., a tear approximately 0 to 1 mm in length). Other tear sizes are also possible. The capsulotomy repair device 901 may be inserted through the same hole in the eye used to insert the main capsularhexis device (e.g., capsularhexis device 10 or another capsularhexis device used to remove the main portion of the lens capsule). In some embodiments, the loop 23 may be aligned with the tear 1051 to slightly overlap the tear 1051 with the broader region of the capsulotomy repair device 901 to create a gradual curved profile on the capsulotomy perimeter 1041. In this way, the entry and exits points 1053a,b of the repair curve 1055 may have a reduced/curved profile (to reduce stress concentrations that may themselves lead to tears).

Figure 11B:
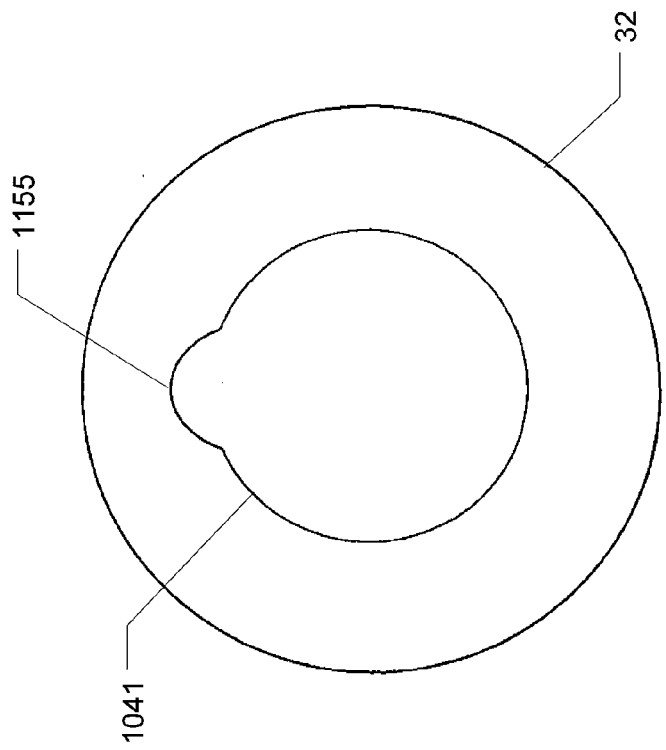
FIGS. 11a-b illustrate a large tear repair using the capsulotomy repair device, according to an embodiment.
Figure 11A:
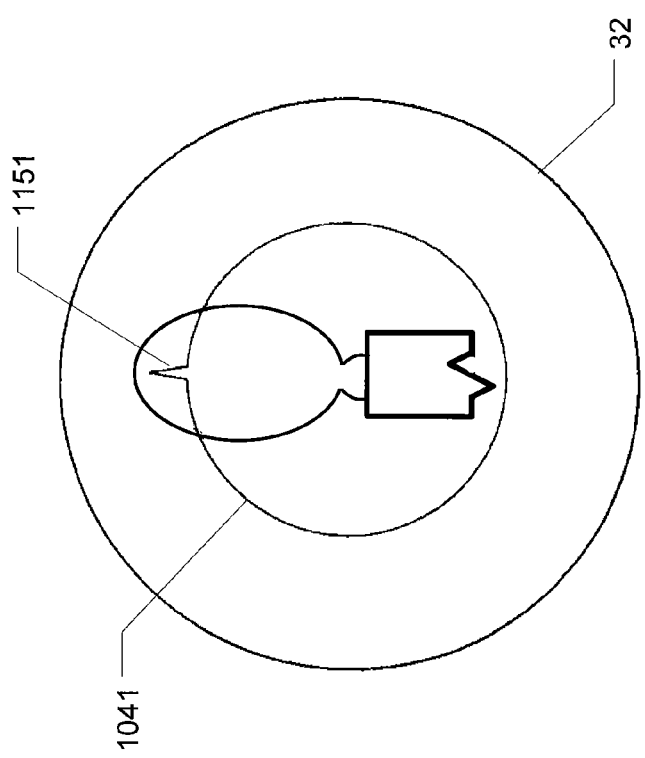

FIGS. 11a-b illustrate an embodiment of a large tear repair using the capsulotomy repair device. FIG. 11a shows the loop 23 of the capsulotomy repair device 901 aligned over an extended tear 1151 (e.g., a tear approximately 1 mm to 2 mm in length) in the lens capsule. Other tear lengths are also possible. The repair curve 1155 may form a substantially continuous curved profile with the capsulotomy perimeter 1041. The narrower region of the oblong heating element loop 903 of the capsulotomy repair device 901 may be used for extended tears 115 to reduce the amount of surrounding material removed during the repair. As noted above, in some embodiments, different loop geometries may be used for different tear sizes (e.g., a more eccentric ellipse-shaped wire may be used for extended tears).

Figure 12:
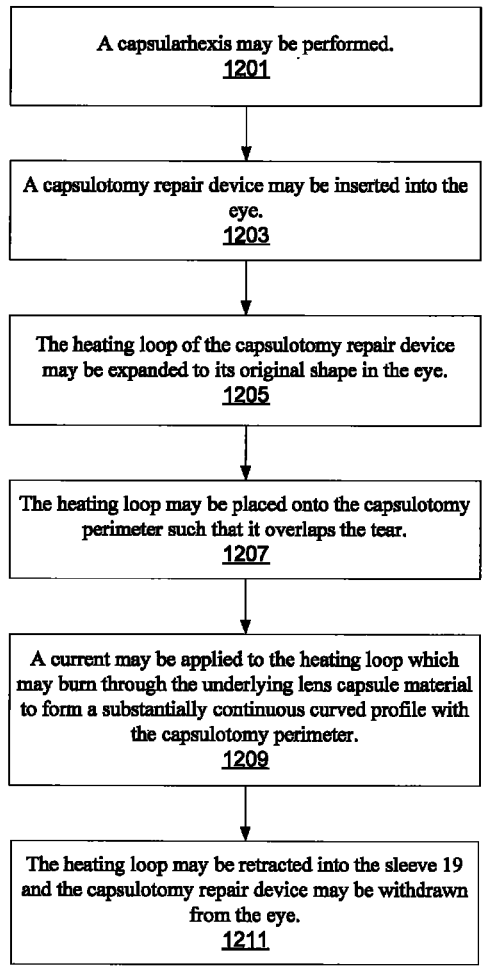
FIG. 12 illustrates a flowchart of a method for capsulotomy repair, according to an embodiment.

FIG. 12 illustrates a flowchart of an embodiment of a method for capsulotomy repair. The elements provided in the flowchart are illustrative only. Various provided elements may be omitted, additional elements may be added, and/or various elements may be performed in a different order than provided below.

At 1201, a capsularhexis may be performed (e.g., according to the method described in FIG. 7). Other methods of performing a capsularhexis are also contemplated (e.g., using a surgical knife). The capsulotomy may include a posterior capsulotomy or an anterior capsulotomy. During the capsularhexis a tear 1051/1151 may form in the capsulotomy perimeter 1041.

At 1203, a capsulotomy repair device 901 may be inserted into the hole used to insert the original capsularhexis device 10. In some embodiments, the capsulotomy repair device 901 may be inserted into a different hole (e.g., a new hole formed for the capsulotomy repair). The loop 23 of the capsulotomy repair device 901 may be retracted into the insertion sleeve 19 during the insertion.

At 1205, the loop 23 of the capsulotomy repair device 901 may be pushed out of the sleeve 19 into the lens capsule and may expand to its original shape (as noted above, the loop 23 may be formed of a superelastic nitinol wire or some other shape memory material). In some embodiments, the loop 23 may be pushed out of the insertion sleeve 19 or the insertion sleeve 19 may be pulled back to expose the loop 23 (e.g., using a lever 45 as seen in FIGS. 2a-b). Other extension methods are also possible (e.g., using a spring or solenoid).

At 1207, the loop 23 may be placed onto the capsulotomy perimeter 1041 such that it overlaps the tear 1051/1151.

At 1209, a current may be applied to the loop 23 which may burn through the underlying lens capsule material to form a substantially continuous curved profile with the capsulotomy perimeter 1041 (e.g., see FIGS. 10b and 11b).

At 1211, the loop 23 may be retracted into the sleeve 19 and the capsulotomy repair device 901 may be withdrawn from the eye. In some embodiments, the loop 23 may be pulled into the insertion sleeve 19 or the insertion sleeve 19 may be pushed over the loop 23 (e.g., using a lever 45 as seen in FIGS. 2a-b). Other retraction methods are also possible (e.g., using a spring or solenoid).

Figure 8:
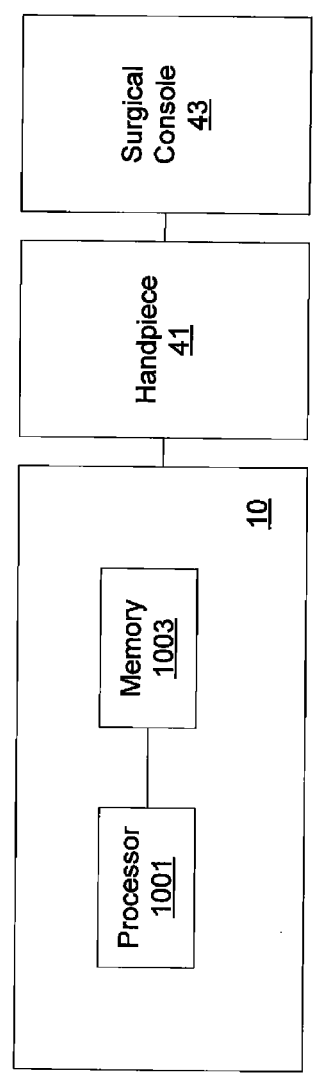
FIG. 8 illustrates a processor and memory for the capsularhexis device, according to an embodiment.

In some embodiments, the capsularhexis device 10 (including the capsulotomy repair device 901) and/or a management system for the capsularhexis device 10 (e.g., handpiece 41 and/or console 43) may include one or more processors (e.g., processor 1001) and/or memories 1003 (e.g., see FIG. 8). The processor 1001 may include single processing devices or a plurality of processing devices. Such a processing device may be a microprocessor, controller (which may be a microcontroller), digital signal processor, microcomputer, central processing unit, field programmable gate array, programmable logic device, state machine, logic circuitry, control circuitry, analog circuitry, digital circuitry, and/or any device that manipulates signals (analog and/or digital) based on operational instructions. The memory 1003 coupled to and/or embedded in the processors 1001 may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processors 1001 implement one or more of its functions via a state machine, analog circuitry, digital circuitry, and/or logic circuitry, the memory 1003 storing the corresponding operational instructions may be embedded within, or external to, the circuitry comprising the state machine, analog circuitry, digital circuitry, and/or logic circuitry. The memory 1003 may store, and the processor 1001 may execute, operational instructions corresponding to at least some of the elements illustrated and described in association with the figures.

Various modifications may be made to the presented embodiments by a person of ordinary skill in the art. For example, although some of the embodiments are described above in connection with capsularhexis devices 10 it can also be used with other thermal surgical devices. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for repairing a capsulotomy in an eye, comprising:
    performing a capsularhexis with a capsularhexis device to form a capsularhexis perimeter in a lens capsule of the eye, wherein the capsularhexis results in at least one tear in the capsularhexis perimeter;
    withdrawing the capsularhexis device from the eye;
    inserting a capsulotomy repair device into the eye;
    positioning a heating loop of the capsulotomy repair device in the eye to overlap a tear of the at least one tear in the capsularhexis perimeter;
    electrically heating the heating loop to burn the lens capsule along the loop; and
    withdrawing the capsulotomy repair device from the eye.

2. The method of claim 1,
    wherein the heating loop is oblong having two extended sides and a narrow tip region.

3. The method of claim 1,
    wherein the heating loop is oblong having two extended sides and a narrow tip region;
    wherein the tear is a large tear and wherein positioning the heating loop comprises positioning the tip to overlap the large tear.

4. The method of claim 1, wherein the capsulotomy repair device comprises an insertion sleeve and wherein the method further comprises:
    ejecting the heating loop from the insertion sleeve in the eye;

retracting the heating loop into the insertion sleeve before removal of the capsulotomy repair device from the eye.

5. A method of claim 1, wherein the heating loop comprises an electrically resistive, superelastic wire having first and second ends, the superelastic wire formed with a loop and a gap between the first and second ends, wherein the first and second ends are adjacent to each other and at least partially extend at an angle from a planar face, defined by the loop to form a transitional neck between the loop and an insulating portion holding the first and second ends.

6. The method of claim 5, wherein at least partially extending at an angle from the planar face defined by the loop comprises extending approximately perpendicular from the planar face defined by the loop.

7. The method of claim 5, wherein at least partially extending at an angle from the planar face defined by the loop comprises extending approximately 45 degrees as measured to a back side of the planar face defined by the loop.

8. The method of claim 5, wherein a gap between the first and second ends at the insulating portion on one side of the transitional neck is wider than the gap between the first and second ends on an opposing side of the transitional neck at the loop.

9. The method of claim 5, wherein the gap between the first and second ends on the opposing side of the transitional neck is at least 0.003 inches.

10. A method for repairing a capsulotomy in an eye, comprising:
    performing a capsularhexis with a capsularhexis device to form a capsularhexis perimeter in a lens capsule of the eye, wherein the capsularhexis results in at least one tear in the capsularhexis perimeter;
    withdrawing the capsularhexis device from the eye;
    inserting a capsulotomy repair device into the eye, wherein the capsulotomy repair device comprises a resistive-heating element comprising an electrically resistive, superelastic wire having first and second ends, the superelastic wire forming a loop with a gap between the first and second ends and an insulating portion comprising an electrically insulating material separating the first and second ends of the superelastic wire, wherein the first and second ends are adjacent to each other and at least partially extend at an angle from a planar face defined by the loop, to the insulating portion, to form a transitional neck between the loop and the insulating portion, wherein the resistive-heating element has a length and width that are smaller than the length and width of the capsularhexis perimeter to be repaired such that the resistive-heating element is configured to overlap a tear in the capsularhexis perimeter for repair of the capsularhexis perimeter;
    positioning the loop of the capsulotomy repair device in the eye to overlap the tear in the capsularhexis perimeter;
    electrically heating the resistive-heating element to burn the lens capsule along the loop; and
    withdrawing the capsulotomy repair device from the eye.

11. The method of claim 10, wherein the resistive heating element comprises an oblong, elliptical shape.

12. The method of claim 10, wherein a length and width of a loop formed by the resistive-heating element are less than 10 mm.

13. The method of claim 10, wherein a length and width of a loop formed by the resistive-heating element are approximately in a range of 3 mm to 7 mm.

14. The method of claim 10, wherein at least partially extending at an angle from the planar face defined by the loop comprises extending approximately perpendicular from the planar face defined by the loop.

15. The method of claim 10, further comprising an insertion sleeve configured to fit around the insulating portion and to substantially contain the resistive-heating element when the resistive-heating element is in a retracted position.

16. The method of claim 10, wherein a gap between the first and second ends at the insulating portion on one side of the transitional neck is wider than a gap between the first and second ends on an opposing side of the transitional neck at the loop.

17. The method of claim 16, wherein the gap between the first and second ends on the opposing side of the transitional neck is approximately 0.003 inches.

18. The method of claim 10, wherein the gap in the loop of superelastic wire is sufficiently small to allow the loop to form a circular, continuous cut in a capsule of an eye when current is applied to the loop while positioned in contact with the capsule.

19. The method of claim 10, wherein the heating loop is oblong having two extended sides and a narrow tip region.

20. The method of claim 10,
    wherein the heating loop is oblong having two extended sides and a narrow tip region;
    wherein the tear is a large tear and wherein positioning the heating loop comprises positioning the tip to overlap the large tear.

* * * * *